United States Patent
Huang et al.

Patent Number: 5,302,022
Date of Patent: Apr. 12, 1994

[54] TECHNIQUE FOR MEASURING THERMAL RESISTANCE OF SEMICONDUCTOR PACKAGES AND MATERIALS

[75] Inventors: Chin-ching Huang, San Jose; Kenny Y. Ng, Union City, both of Calif.

[73] Assignee: VLSI Technology, Inc., San Jose, Calif.

[21] Appl. No.: 995,236

[22] Filed: Dec. 22, 1992

[51] Int. Cl.$^5$ .................................... G01N 25/18
[52] U.S. Cl. ............................... 374/44; 374/43
[58] Field of Search ............................ 374/43, 44

[56] References Cited

U.S. PATENT DOCUMENTS 4,734,641  3/1988  Byrd, Jr. et al. ............... 374/44 X

FOREIGN PATENT DOCUMENTS 2592490  7/1987  France ............................. 374/43
0161649  12/1981  Japan ............................... 374/43

OTHER PUBLICATIONS

Rodkey D. L., Manual For Using Delco Electronics Thermally Sensitive Die Jan. 1987 pp. 3, 4, 7 and 13.
John H. Lau, *"Handbook of Tape Automated Bonding"* Multichip Modules With TAB: Issues p. 475 Multichip Modules and TAB in Practice p. 485.

*Primary Examiner*—William A. Cuchlinski, Jr.
*Assistant Examiner*—W. Morris Worth
*Attorney, Agent, or Firm*—Majestic, Parsons, Siebert & Hsue

[57] ABSTRACT

A thermal test apparatus for measuring the thermal heat transfer characteristics of semiconductor packaging material as well as the thermal characteristics of the package design is disclosed comprising a substrate having the size and shape of a semiconductor die. The substrate is in contact with the semiconductor packaging material. A heating source for heating the substrate is located within the apparatus, along with a temperature sensitive element for which the voltage drop across the element is a function of temperature. The element is connected in series via a first set of conductive traces to forcing pads used to force current through the element. Sensing pads for measuring the forward voltage drop of the diode are connected in parallel via a second set of conductive traces across the element to two points very close to the element in order to greatly reduce the thermal resistance measurement error due to the resistance in the conductive trace material. In another aspect of the present invention the thermal measurement error is reduced by connecting the sensing pads via a second set of conductive traces to two points across the diode such that those two points are located not more than two microns from the diode. Once the voltage drop across the element is measured, the temperature of the element and the junction surrounding the element can be determined and standardized to indicate the relative thermal conductive properties of the various semiconductor designs and packaging materials used.

8 Claims, 4 Drawing Sheets

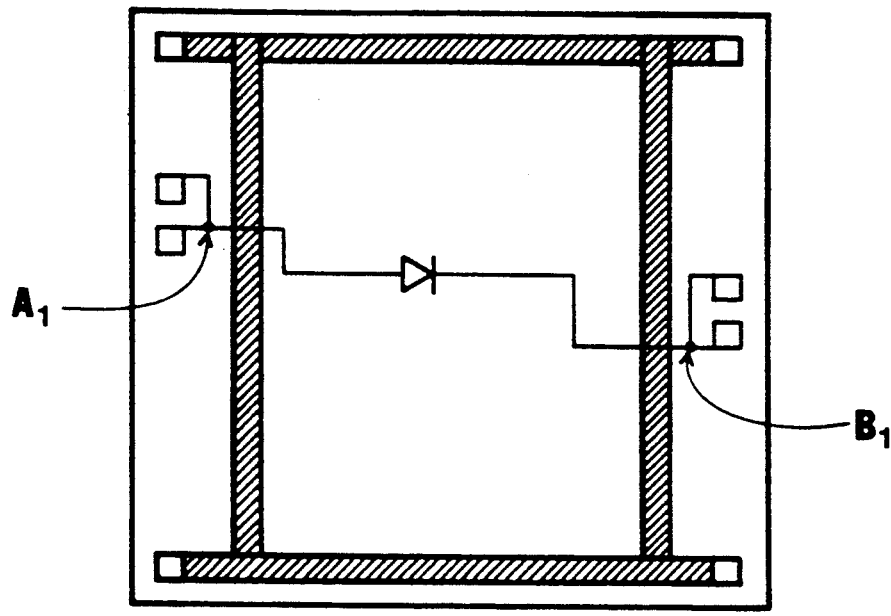
Fig.—1.
Prior Art
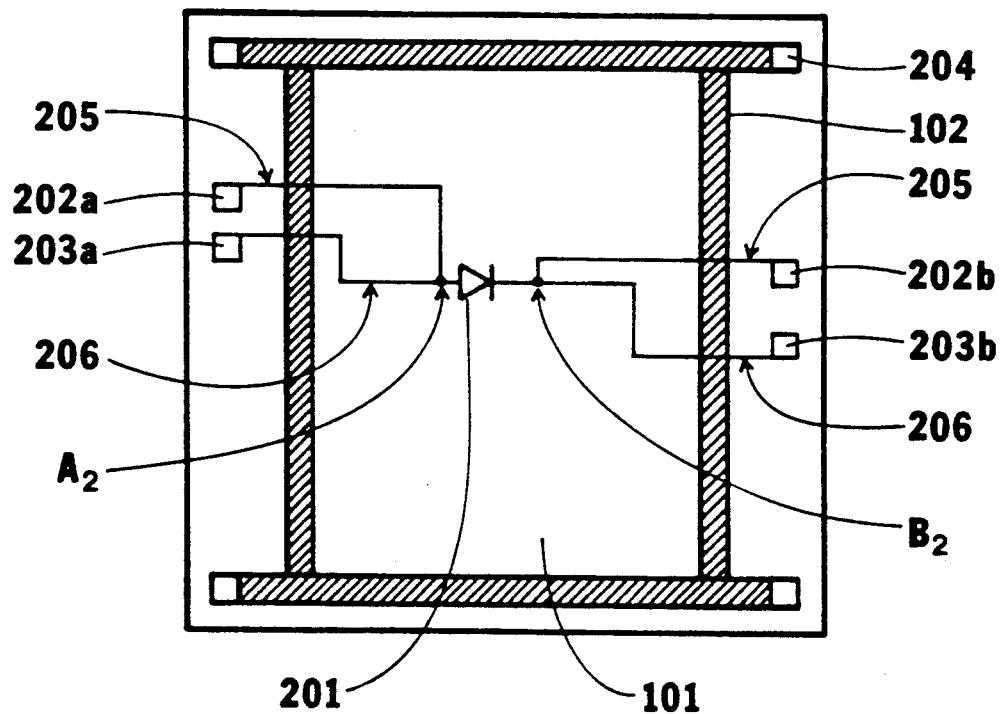
Fig.—2.

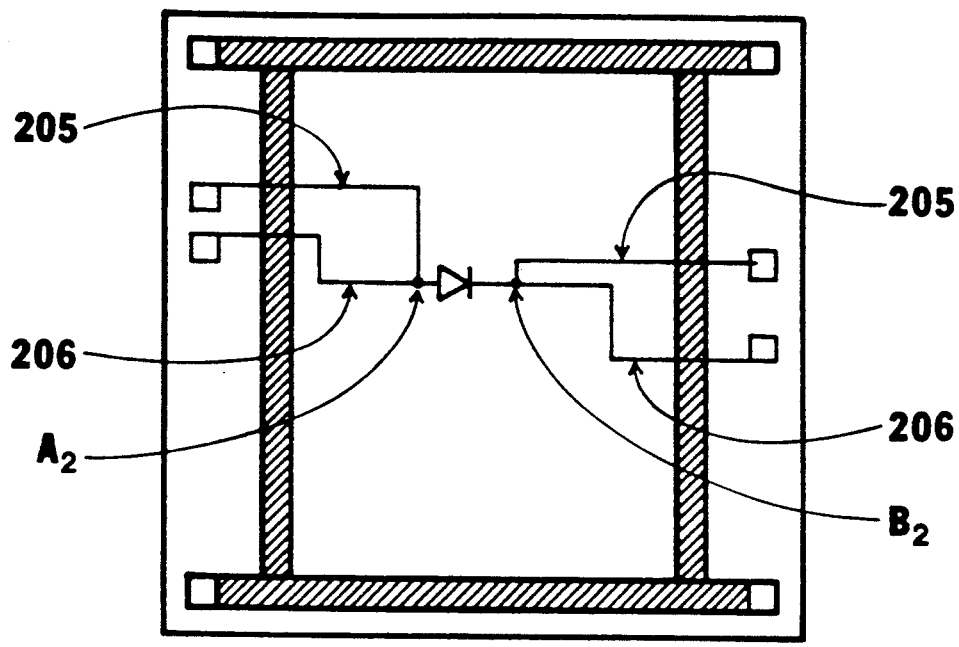
Fig.—3.
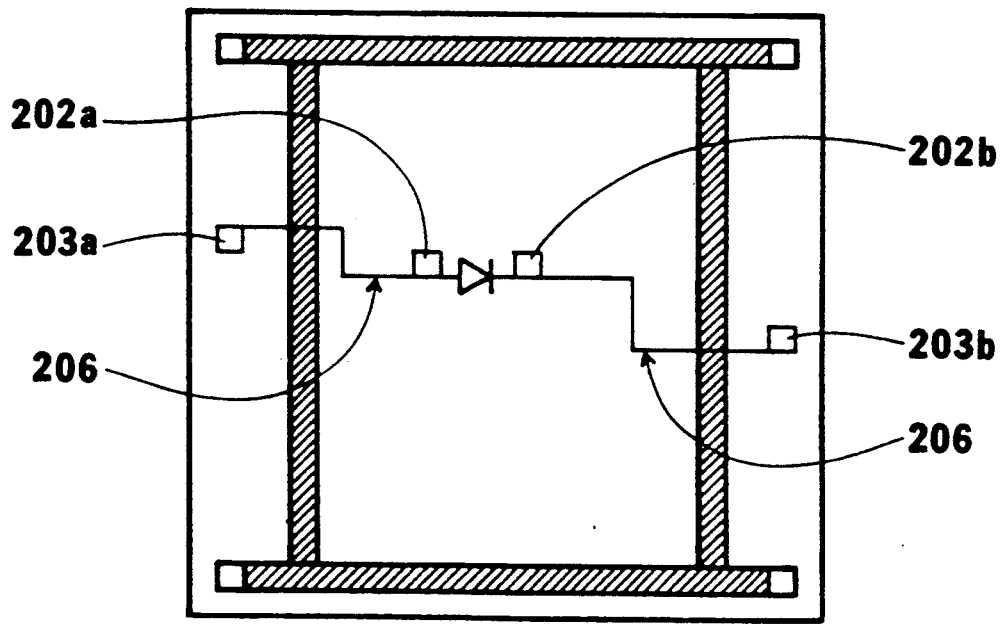
Fig.—4.

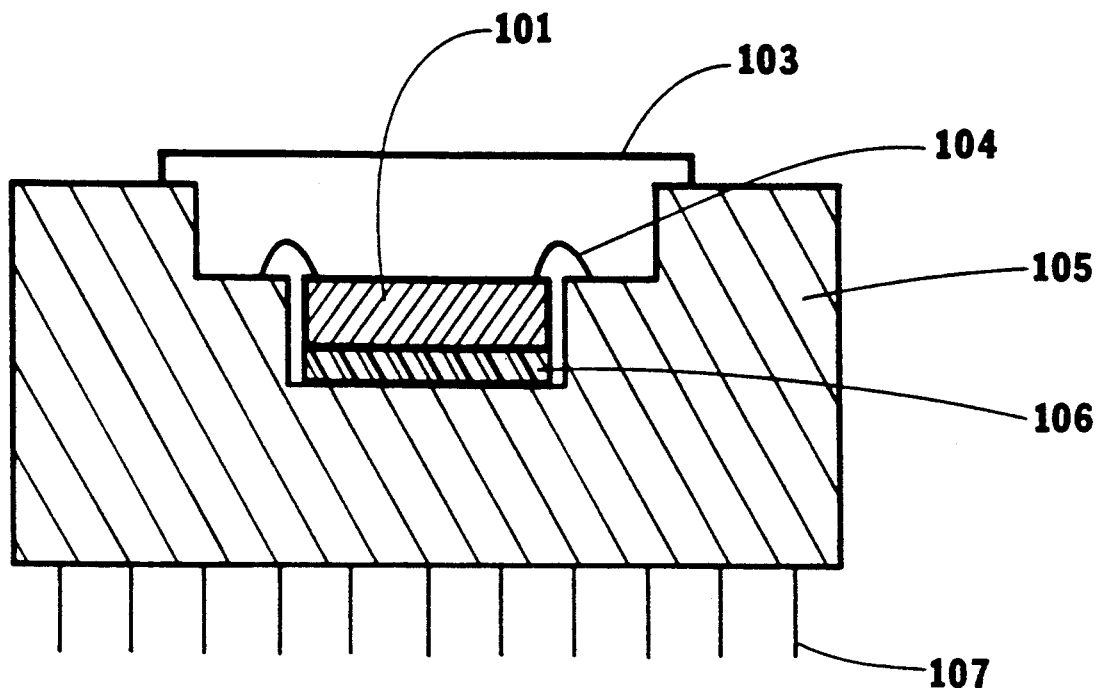
Fig.—5.
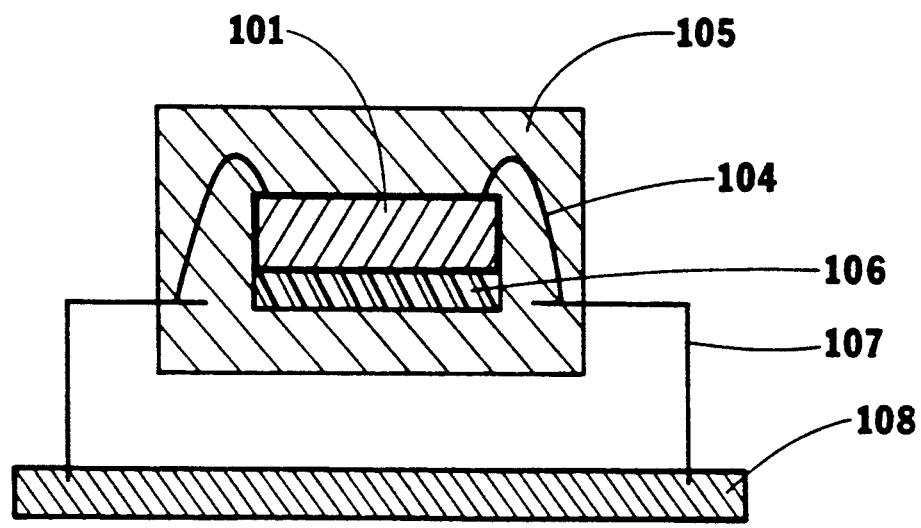
Fig.—6.

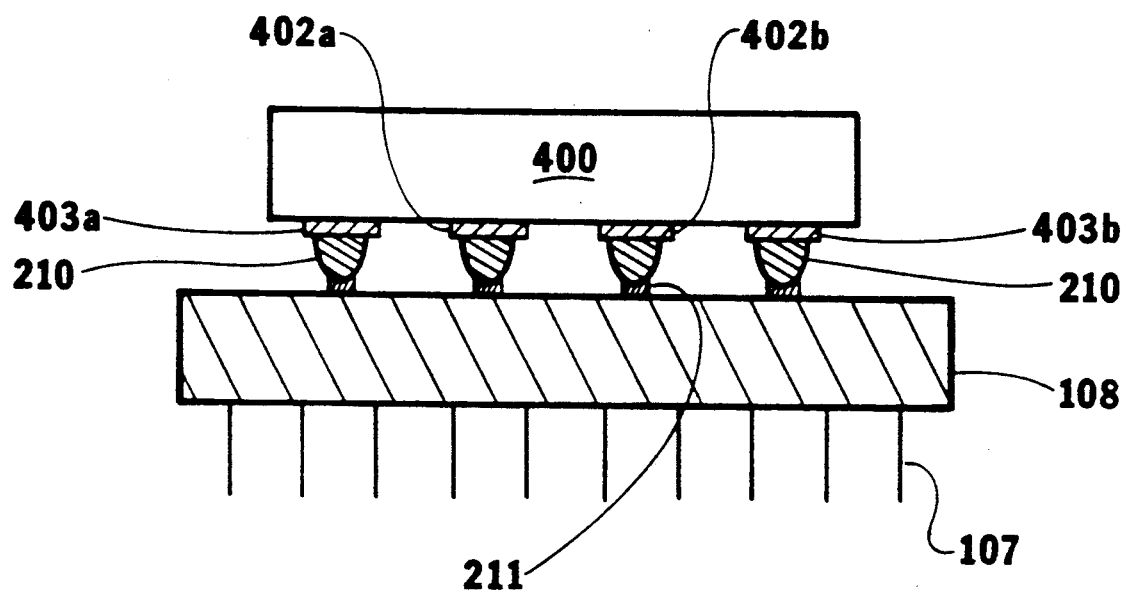
Fig. __7.
Prior Art

TECHNIQUE FOR MEASURING THERMAL RESISTANCE OF SEMICONDUCTOR PACKAGES AND MATERIALS

FIELD OF THE INVENTION

The present invention relates broadly to the field of semi-conductor manufacture and use, and particularly to a new layout of thermal test die to improve the accuracy of the measurement of thermal characteristics of semi-conductor packaging material.

BACKGROUND OF THE INVENTION

As the ability to reduce the physical size of semi-conductor circuits has increased, there exists a corresponding need to dissipate the power generated from these circuits. Effective cooling is required in situations involving high circuit density in order to maintain chip operating temperatures at acceptable levels. Therefore, there has been an ever increasing need to improve the heat transfer characteristics of semi-conductor packaging material.

Various techniques are available for measuring the thermal-characteristics of the packaging material used to package semi-conductor chips. One common technique is the use of a thermal test die as disclosed in *Manual for Using Delco Electronics Thermally Sensitive Die*, by D. L. Rodkey, Jan. 30, 1987. The apparatus disclosed within this manual relates to measuring the thermal resistance of semiconductor packaging material. In that apparatus, a test die consisting of an isolated diode, conductive traces, and heating elements are placed within semi conductor packaging material having the size and shape of a semi conductor chip. A fixed current is forced through the isolated diode, causing a fixed forward voltage drop across that diode. The heating element is then activated, causing the test die and the diode to heat up. As known to one skilled in the relevant art, the forward voltage drop of a diode changes in response to the temperature of that diode. For the apparatus disclosed in the Delco manual, the heat generated in the test die will cause a decrease in the forward voltage drop of the diode by 2 mV for each degree Celsius rise in temperature. The calculations from which this equation is derived are located in the Delco manual, page 3. Sensing pads are attached in parallel across the diode to measure the decrease in the forward voltage drop of the diode as due to the heat generated by the heating element. The better the thermal conductive properties of the semiconductor packaging material, the greater the power dissipation of that material, resulting in a lower decrease in the forward voltage drop of the diode.

A common problem which plagues this type of test die is its inaccuracy resulting from voltage drops caused by resistance in the trace material. In theory, the decrease in the forward voltage drop of the diode should be due purely to the rise in temperature of the diode. However, in reality, the voltage drop across the diode as measured at the sensing pads necessarily includes an error attributed to the resistance in the conductive trace. As commonly known to one skilled in the art, current passing through a resistive element will experience a voltage drop. Since a constant current is forced through the first set of conductive traces connecting the forcing pads to the diode, the resistance contained in the first set of traces results in a voltage drop along those traces. Thus, the sensing pads which are connected via a second set of conductive traces to the first set of conductive traces measure not only the forward voltage drop across the diode, but also the voltage drop due to the resistance in the first set of conductive traces. Depending upon the size of the die and the thickness of the conductive trace used, errors in excess of 44 percent have been calculated when measuring the forward voltage drop of the diode. This error ratio, known as thermal resistance measurement error, is attributable to the resistance in the first set of conductive traces which connect the forcing pads to the diode. The resistance contained in this first set of traces becomes significant because of the amount of current which is being forced through those traces.

Thus the thermal test die apparatus which is available for measuring the thermal characteristics of various semiconductor packaging materials has not proved to be as accurate as is desired.

SUMMARY OF THE INVENTION

In view of the problems associated with the above testing apparatus, it is the primary object of the present invention to minimize the thermal resistance measurement error by using a new design layout for the thermal test die. This new design results in a highly accurate device for measuring the thermal heat transfer characteristics of semi conductor packaging material as well as the thermal characteristics of the package design.

In accomplishing these and other objectives of the invention, the present invention is directed to an apparatus for measuring the thermal characteristics of semi conductor packaging material. The apparatus is comprised of a substrate having the size and shape of a semiconductor die. The substrate is in contact with the semiconductor packaging material. A heating source for heating the substrate is located within the apparatus, as well as a temperature sensitive element for which the voltage drop across the element is a function of temperature. In the preferred embodiment, this element is an isolated diode. The diode is connected in series via a first set of conductive traces to forcing pads used to force current through the diode. The apparatus further comprises sensing pads for measuring the forward voltage drop of the diode. These pads are connected in parallel across the diode via a second set of conductive traces.

As mentioned previously, significant errors have been encountered when measuring the thermal resistance of semiconductor packaging material due to the resistance of the first set of conductive traces. In one aspect of the present invention the thermal resistant measurement error is reduced to a ratio of not more than 5 percent. In another aspect of the present invention the thermal measurement error is reduced by connecting the sensing pads via a second set of conductive traces to two points across the diode such that those two points are located not more than two microns from the diode. Previously, the sensing pads were connected via a second set of conductive traces to two points on the first set of conductive traces very close to the forcing pads and further away from the diode. By connecting the sensing pads to points very close to the forcing pads, the voltage drop across a large portion of the first set of conductive trace with constant current running through it was included in the measurement of the voltage drop across the diode. This excess amount of conductive trace accounted for the large thermal resistant measurement error as previously mentioned. The present invention avoids the unnecessary inclusion of this excess conductive trace by attaching the sensing pads via the second set of conductive traces to points very close to the diode, thus eliminating nearly all of the erroneous voltage drop previously measured at the sensing pads. Although lengthened portions of the second set of conductive traces are needed to achieve this new connection, there is only a minimal amount of current which runs through these traces, since they are used for measuring the voltage drop across the diode and not for forcing current through the diode. Thus the lengthening of these conductive traces does not contribute significantly to the measurement error of the forward voltage drop across the diode. In another aspect of the present invention, the sensing pads are attached directly to the first set of conductive traces across the diode at the same points where the second set of conductive traces would be attached, eliminating any thermal measurement error contributed by the second set of conductive traces. In fact, by attaching the sensing pads either directly or via the second set of conductive traces to points very close to the diode, a lower thermal resistance measurement error is achieved, resulting in a highly accurate device for measuring the thermal heat transfer characteristics of semi conductor packaging material as well as the thermal characteristics of the package design.

Another aspect of the present invention is directed to a method for measuring the thermal resistance of semiconductor packaging material. This method comprises the steps of placing a temperature sensitive element, such as an isolated diode or a plurality of isolated diodes connected in series, and a heating element within a substrate. The substrate is usually a thermal test die. The substrate, along with the diode and the heat source, are placed in contact with the semiconductor packaging material. The diode is then connected via a first set of conductive traces to forcing pads located external to the packaging material. A second set of conductive traces are then connected to sensing pads located external to the packaging material. The other end of the second set of traces is connected to the first set of conductive traces such that the ratio of the voltage drop across the due to the resistance of the first set of conductive traces to the voltage drop across the diode is not more than 5%. In the preferred embodiment of this method, this means that the points connecting the second set of conductive traces to the first set should be as close as possible to the diode, or temperature sensitive element. A constant current is then forced through the diode via the first set of conductive traces. The packaging material is then heated by activating the heat source. Lastly, the forward voltage drop across the diode is measured at the sensing terminal, from which the thermal characteristics of the packaging material can be determined.

After the above procedure has been followed and the voltage drop across the diode has been taken, it is then possible to calculate the temperature of the junction where the die and the semiconductor packaging material meet. Since the current which is forced through the diode is held constant, the voltage drop across the diode is held to a theoretical constant at a constant temperature. Any measurable voltage drop in excess of this theoretical constant is attributed to the temperature diode, which is assumed to be the temperature of the junction surrounding the diode. Therefore, by knowing the voltage drop across the diode, one is able to calculate the temperature of the junction at which the thermal test die and semiconductor packaging material meet. This temperature then is used to rate the thermal characteristics of the semiconductor packaging material used in that test.

Thus the apparatus as disclosed in the present application allows for precisely measuring the thermal characteristics of semiconductor packaging material with a much lower thermal resistance measurement error than that of the prior art. Furthermore, the present invention measures not only the thermal conductive properties of semiconductor packaging material but also the properties of the packaging structure itself. Therefore, the apparatus as disclosed in the present invention may be used to evaluate packages and materials such as a ceramic pin grid array (CPGA), a plastic pin grid array (PPGA), a multi-chip module, a molded quad flat pack (MQFP), and a plastic lead chip carrier (PLCC).

BRIEF DESCRIPTION OF THE DRAWINGS

The foregoing and other objects, advantages and features of the present invention are described below in greater detail in connection with the drawings which form a part of the disclosure wherein:

FIG. 1 is a top view of the layout of a conventional thermal test die;

FIG. 2 is a top view of the new layout for a thermal test die as disclosed in the present application;

FIG. 3 is a top view of an alternate method of the new layout using wider trace material;

FIG. 4 is a top view of the new layout for area array chips;

FIG. 5 is a cross sectional view of the new apparatus which consists of the thermal test die packaged in a pin grid array; and FIG. 6 is a cross sectional view of the new layout which consists of a thermal test die packaged in a molded quad flat pack.

FIG. 7 is a cross sectional view of an area array chip connected to a PC board to illustrate the standard technique for electrically connecting an area array chip to a substrate.

DETAILED DESCRIPTION OF THE PREFERRED EMBODIMENT

FIGS. 1 and 2 illustrate the differences between the conventional thermal test die and the new layout of the thermal test die as disclosed in the present application. FIG. 2 is an illustration of the preferred embodiment of the new layout of the thermal test die. FIG. 2 shows various components of the new layout attached to a substrate structure 101. This substrate structure 101 typically will have the size and shape of a semiconductor die, which usually ranges from an area of 150 mils by 150 mils to an area of 250 mils by 250 mils. The size and shape of the die however may be varied to accommodate any number of required specifications.

Attached to the substrate structure 101 of FIG. 2 are the heating source 102, the isolated diode 201, the sensing pads 202a and 202b, the forcing pads 203a and 203b, a first set of conductive traces 206, and a second set of conductive traces 205. The heat source 102 as depicted in FIG. 2 is a set of resistive traces arranged uniformly around the diode 201 so that even heat distribution can be achieved. The heat source 102 may also be resistive elements made of resistive trace, resistors which are passive elements, or a functional active device such as a working circuit surrounding an isolated diode where the functional active device operates to heat the junction of the diode, or any combination thereof. The temperature sensitive element 201 may be an isolated diode or a plurality of isolated diodes connected in series. The sensitivity of one diode for thermal measurement is about two millivolts per degree celsius. This sensitivity can be improved to 10 millivolts per degree celsius by connecting a plurality of 5 isolated diodes in series. The greater the number of diodes connected in series the lower the sensitivity of the test die to outside noise. Therefore, one method to reduce the thermal resistant measurement error is to connect a plurality of isolated diodes in series thereby reducing proportionally the significance of the voltage drop due to the resistance in the first set of conductive traces 206.

As depicted in FIG. 2, the first set of conductive traces 206 connect the diode 201 to forcing pads 203a and 203b. The conductive trace may be made of aluminum or of a titanium-tungsten combination, or of gold. The forcing pads 203a and 203b are used to force current through the diode 201 via the first set of conductive traces 206. The current forced through the diode is kept constant, typically at about 100 micro amps, which in turn produces a forward voltage drop across the diode. Sensing pads 202a and 202b are used to measure this forward voltage drop. The sensing pads 202a and 202b are connected via second set of conductive traces 205 to the first set of conductive traces 206. As depicted in the prior art of FIG. 1, the points wherein the second set of conductive traces are connected to the first set of conductive traces are referenced as points $A_1$ and $B_1$ respectively. In FIG. 1, it can clearly be seen that a large portion of the first set of conductive traces is included between reference points $A_1$ and $B_1$. Since a steady current is continually flowing in the conductive trace between points $A_1$ and $B_1$, there will be a voltage drop attributable to the resistance in the conductive trace between those two points. Insofar as the voltage drop attributable to the conductive trace may change differently from that attributable to the diode, this design contributes significantly to thermal measurement error of the apparatus. The new layout of FIG. 2, however, avoids the unnecessary inclusion of this excess conductive trace 206 between points $A_1$ and $B_1$ by repositioning the location where the second set of conductive traces 205 attached to the first set of conductive traces 206. These new points are referred to in FIG. 2 as references points $A_2$ and $B_2$, and are located on the first set of conductive traces 206 such that the ratio of the voltage drop across the two points $A_2$ and $B_2$ due to the resistance of the first set of conductive traces to the voltage drop across the diode is not more than 5 percent. Typically, where one diode is used as the temperature sensitive element, the distance from point $A_2$ and point $B_2$ to the diode are not more than 2 microns respectively. It is noted that in FIG. 2 the length of the second set of conductive traces 205 has been extended when compared to the length of the traces in FIG. 1. However, the extension of the traces 205 does not result in a significant increase in the thermal measurement error since the traces 205 have only a minimal amount of current running through them to measure the voltage drop across the diode, whereas the traces 206 have a constant and steady current running through them so as to force a forward voltage drop across the diode.

FIG. 3 depicts an alternate method to reduce the thermal temperature measurement error by using wider metal trace for the conductive trace materials 205 and 206. A wider metal trace will correspondingly contain less resistance and therefore will generate a lower voltage drop when current is forced through the trace. Thus FIG. 3 contains the same modification of reference points $A_2$ and $B_2$ as does FIG. 2 when compared to the prior art, and in addition, uses wider conductive trace material to further reduce the inclusion of any error due to voltage drop caused by the resistance in the conductive trace material.

FIG. 4 is a different version of the preferred embodiment whereby the sensing pads 202a and 202b are located directly on the first set of conductive traces 206 precisely where reference points $A_2$ and $B_2$ would be located respectively in FIG. 2. This alternate layout is specifically intended for use with area array chips.

As commonly known to those skilled in the art, FIG. 7 illustrates how an area array die 400, such as the test die of FIG. 4, is attached to a printed circuit board 108. As illustrated in FIG. 7, sensing pads 402a and 402b and bonding pads 403a and 403b are bonded directly to printed circuit board bonding pads 211 via conductive bumps 210.

FIG. 5 illustrates the test die of FIG. 2 within a pin grid array package, where said semiconductor packaging material is made of either ceramic or plastic. As illustrated in FIG. 5, the substrate structure 101 is attached to the semiconductor packaging material 105 via a die attach area 106. The die attach area may be comprised of epoxy, a gold silicon die attach made of 98 percent gold and 2 percent silicon, or a silver glass combination. Wires 104 connect the sensing pads 202a and 202b, forcing pads 203a and 203b, and heat source bonding pads 204 to metal leads or pins 107 located external to the packaging material 105. The configuration in FIG. 5 also contains a lid 103 for covering the thermal test die. The configurations of the ceramic pin grid array package (CPGA) and the plastic pin grid array package (PPGA) are both known to those skilled in the relevant art, and therefore no further disclosure is necessary in this application.

FIG. 6 illustrates the thermal test die within a molded quad flat pack (MQFP). This configuration is similar to that of FIG. 5 in that the substrate structure 101 is attached to the semiconductor packaging material 105 via a die attach area 106. Wires 104 connect the sensing pads 202a and 202b, forcing pads 203a and 203b, and heat source bonding pads 204 to metal leads and pins 107 located external to the packaging material 105. The metal leads 107 are typically attached to a printed circuit board 108. The configuration of the molded quad flat pack is commonly known to ones skilled in the art and therefore further enablement in this application is unnecessary.

After the thermal test die has been configured in accordance with the aforementioned preferred embodiment, the operation of the apparatus is relatively straight forward. Current is first applied to the metal leads 107 which are connected via wires 104 to the forcing pads 203a and 203b, which in turn forces current through the first set of conductive traces 206 and through the diode 201 causing a forward voltage drop across that diode. The current flow is kept to an exact constant, typically at about 100 micro amps, so as to insure that any forward voltage drop fluctuation across the diode is not due to a change in current running through that diode. Current is then applied to the appropriate metal leads 107 which are connected by wires 104 to the heat source bonding pads 204, which in turn activates the heat source 102, heating the substrate structure 101 and the semiconductor packaging material 105. Measurements are then taken at the metal leads 107 which are connected by a wire 104 to the sensing pads 202a and 202b, which measure the voltage drop across the diode as a function of the temperature of the area surrounding the diode. The thermal conductive properties of the semiconductor packaging material 105 are then calculated by determining the temperature of diode, which is assumed to be the same as the temperature of the junction surrounding the diode. For each unit of degree celsius rise there will be a corresponding drop in the forward voltage across the diode of 2 millivolts. Therefore, the better the thermal conductive properties of the semiconductor packaging material 105, the more power that packaging material will be able to dissipate. This results in a lower temperature of the junction surrounding the diode, for which a higher voltage drop across the diode will be measured.

The thermal characteristics of each semiconductor packaging material and the package itself are then standardized by subtracting the ambient temperature ($T_A$) which is the temperature of the outside surface of the packaging material from the junction temperature ($T_J$) which is the temperature at the surface of the substrate structure wherein the diode is located, and dividing this result by the power supplied to the heating source. This equation—$(T_J-T_A)$/(power of heat source)—is equal to the thermal resistent measurement or Theta $J_A$ of the semiconductor package and material. This information as well as the complete operating procedure for the thermal test die is located in the *Manual for using delco electronics thermally sensitive die*, by D. L. Rodkey, Jan. 30, 1987, and need not be discussed further in the present application.

From the foregoing description including various modifications to the preferred embodiment as illustrated in the drawings, it will be clear to those skilled in the art that numerous modifications may be made to the apparatus herein described without departing from the spirit and scope of the present invention as defined in the following claims.

It is claimed:

1. An apparatus for measuring the thermal characteristics of semiconductor packaging material, said apparatus comprising:
    a substrate in contact with said semiconductor packaging material;
    a heat source for heating the substrate;
    a temperature sensitive element on or in said substrate wherein the voltage drop across the element is a function of temperature;
    sensing terminals for measuring the voltage across the element;
    forcing terminals for forcing current through the element;
    a first set of conductive traces connecting the forcing terminals to the element for forcing current through said element;
    a second set of conductive traces connecting the sensing terminals to said first set of conductive traces at two points across the element for measuring the voltage across the element, each of said two points located such that the ratio of the voltage drop across the two points due to the resistance of the first set of conductive traces to the voltage drop across the element is not more than 5%.

2. The apparatus of claim 1 wherein said temperature sensitive element is an isolated diode.

3. The apparatus of claim 1 wherein said temperature sensitive element is a plurality of n isolated diodes connected in series between said two points.

4. The apparatus of claim 3 wherein the ratio of the voltage drop across the two points due to the resistance of the first set of conductive traces to the voltage drop across the plurality of n isolated diodes is not more than 8/n percent.

5. An apparatus for measuring the thermal characteristics of semiconductor packaging material, said apparatus comprising:
    a substrate in contact with said semiconductor packaging material;
    a heat source for heating the substrate;
    a temperature sensitive element on or in said substrate wherein the voltage drop across the element is a function of temperature;
    sensing terminals for measuring the voltage across the element;
    forcing terminals for forcing current through the element;
    a first set of conductive traces connecting the forcing terminals to the element for forcing current through said element;
    a second set of conductive traces connecting the sensing terminals to said first set of conductive traces at two points across the element for measuring the voltage across the element such that each of said two points are located not more than 2 microns from the element.

6. An apparatus for measuring the thermal characteristics of semiconductor packaging material, said apparatus comprising:
    a substrate in contact with said semiconductor packaging material;
    a heat source for heating the substrate;
    a temperature sensitive element on or in said substrate wherein the voltage drop across the element is a function of temperature;
    forcing terminals for forcing current through the element;
    a first set of conductive traces connecting the forcing terminals to the element for forcing current through said element;
    sensing terminals for measuring the voltage across the element connected to said first set of conductive traces at two points across the element for measuring the voltage across the element, each of said two points located such that the ratio of the voltage drop across the two points due to the resistance of the first set of conductive traces to the voltage drop across the element is not more than 5%.

7. A method for measuring the thermal resistance of semiconductor packaging material, comprising the steps of:
    placing a temperature sensitive element within a substrate in contact with said semiconductor packaging material, wherein the voltage drop across the element is a function of temperature;
    connecting the element in series to forcing terminals located external to the packaging material by means of a first set of conductive traces;
    connecting a second set of conductive traces to the first set of conductive traces at two points across the element such that the ratio of the voltage drop across the two points due to the resistance of the first set of conductive traces to the voltage drop across the element is not more than 5%;

connecting the second set of conductive traces to sensing terminals located external to the packaging material;

forcing current through the element wherein the current is applied to the forcing terminals and travels through the first set of conductive traces;

heating the semiconductor packaging material with a heat source contained within said substrate;

measuring the voltage drop across the element at said sensing terminals.

8. A method for measuring the thermal resistance of semiconductor packaging material, comprising the steps of:

placing a temperature sensitive element within a substrate in contact with said semiconductor packaging material, wherein the voltage drop across the element is a function of temperature;

connecting the element in series to forcing terminals located external to the packaging material by means of a first set of conductive traces;

connecting a second set of conductive traces to the first set of conductive traces at two points across the element such that the ratio of the voltage drop across the two points due to the resistance of the first set of conductive traces to the voltage drop across a plurality of n isolated diodes is not more than 8/n percent;

connecting the second set of conductive traces to sensing terminals located external to the packaging material;

forcing current through the element wherein the current is applied to the forcing terminals and travels through the first set of conductive traces;

heating the semiconductor packaging material with a heat source contained within said substrate;

measuring the voltage drop across the element at said sensing terminals.

* * * * *